United States Patent
Parry et al.

(10) Patent No.: US 10,413,426 B2
(45) Date of Patent: Sep. 17, 2019

(54) SPINAL IMPLANT CONFIGURED FOR MIDLINE INSERTION AND RELATED INSTRUMENTS

(71) Applicant: Centinel Spine, Inc., New York, NY (US)

(72) Inventors: John Parry, West Chester, PA (US); John J. Viscogliosi, New York, NY (US)

(73) Assignee: CENTINEL SPINE, LLC, New York, NY (US)

( * ) Notice: Subject to any disclaimer, the term of this patent is extended or adjusted under 35 U.S.C. 154(b) by 0 days.

(21) Appl. No.: 15/428,601

(22) Filed: Feb. 9, 2017

(65) Prior Publication Data

US 2017/0239061 A1    Aug. 24, 2017

Related U.S. Application Data

(63) Continuation of application No. 14/215,718, filed on Mar. 17, 2014, now Pat. No. 9,566,166.
(Continued)

(51) Int. Cl.
| | | |
|---|---|---|
| *A61F 2/44* | (2006.01) | |
| *A61F 2/30* | (2006.01) | |
| *A61F 2/46* | (2006.01) | |
| *A61B 17/16* | (2006.01) | |
| *A61B 17/88* | (2006.01) | |

(52) U.S. Cl.
CPC ........ *A61F 2/4611* (2013.01); *A61B 17/1604* (2013.01); *A61F 2/30771* (2013.01); *A61F 2/44* (2013.01); *A61F 2/442* (2013.01); *A61F 2/447* (2013.01); *A61F 2/4455* (2013.01); *A61F 2/4637* (2013.01); *A61B 17/1642* (2013.01); *A61B 17/1671* (2013.01);
(Continued)

(58) Field of Classification Search
CPC .. A61F 2/46; A61F 2/4611; A61F 2002/4615; A61F 2002/4619; A61F 2002/4623; A61F 2002/4625
See application file for complete search history.

(56) References Cited

U.S. PATENT DOCUMENTS

| | | |
|---|---|---|
| 5,624,106 A | 4/1997 | Weber |
| 7,662,175 B2 | 2/2010 | Jackson |

(Continued)

FOREIGN PATENT DOCUMENTS

| | | |
|---|---|---|
| EP | 2361572 A1 | 8/2011 |
| EP | 2508150 A1 | 10/2012 |
| WO | 2011057181 A1 | 5/2011 |

OTHER PUBLICATIONS

Extended European Search Report dated Sep. 13, 2016, European Application No. 14763222, filed Mar. 17, 2014, pp. 1-7.
(Continued)

*Primary Examiner* — Christian A Sevilla
(74) *Attorney, Agent, or Firm* — Farber LLC; Tram Anh Nguyen

(57) ABSTRACT

The embodiments provide a spinal implant that is configured for midline insertion into a patient's intervertebral disc space. The spinal implant may include structural guidance features to facilitate the angular approach of fixation elements into the apertures. The spinal implant may also be a configured with a tactile or visual feedback response feature to allow the user to know when the fixation elements are fully seated within the apertures.

15 Claims, 8 Drawing Sheets

Related U.S. Application Data

(60) Provisional application No. 61/793,847, filed on Mar. 15, 2013.

(52) U.S. Cl.
CPC ... *A61B 17/8875* (2013.01); *A61F 2002/3008* (2013.01); *A61F 2002/30062* (2013.01); *A61F 2002/3079* (2013.01); *A61F 2002/3093* (2013.01); *A61F 2002/30787* (2013.01); *A61F 2002/30841* (2013.01); *A61F 2002/30879* (2013.01); *A61F 2002/30884* (2013.01); *A61F 2002/4475* (2013.01); *A61F 2002/4638* (2013.01); *A61F 2310/00005* (2013.01); *A61F 2310/00017* (2013.01); *A61F 2310/00023* (2013.01)

(56) References Cited

U.S. PATENT DOCUMENTS

| | | |
|---|---|---|
| 7,914,559 B2 | 3/2011 | Carls et al. |
| 8,740,983 B1* | 6/2014 | Arnold .................. A61F 2/4455 623/17.16 |
| 8,840,668 B1 | 9/2014 | Donahoe et al. |
| 2003/0083747 A1* | 5/2003 | Winterbottom ........... A61F 2/28 623/17.11 |
| 2004/0236333 A1 | 11/2004 | Lin |
| 2009/0264927 A1 | 10/2009 | Ginsberg et al. |
| 2011/0166611 A1 | 7/2011 | Stinson |
| 2011/0166656 A1 | 7/2011 | Thalgott et al. |
| 2011/0166657 A1 | 7/2011 | Thalgott et al. |
| 2011/0313528 A1 | 12/2011 | Laubert |
| 2012/0078373 A1 | 3/2012 | Gamache et al. |
| 2012/0197317 A1* | 8/2012 | Lezama ................ A61F 2/4611 606/86 A |
| 2012/0277870 A1 | 11/2012 | Wolters |

OTHER PUBLICATIONS

International Search Report and Written Opinion for PCT/US2014/030251 dated Aug. 27, 2014.

* cited by examiner

SPINAL IMPLANT CONFIGURED FOR MIDLINE INSERTION AND RELATED INSTRUMENTS

CROSS-REFERENCE TO RELATED APPLICATIONS

This application is a continuation of U.S. patent application Ser. No. 14/215,718, filed Mar. 17, 2014 (allowed), which application claims benefit of U.S. Provisional No. 61/793,847, filed Mar. 15, 2013, and entitled "SPINAL IMPLANT CONFIGURED FOR MIDLINE INSERTION AND RELATED INSTRUMENTS," the entire contents of which are herein incorporated by reference.

FIELD

The present disclosure relates to orthopedic implants, and more particularly, to spinal implants that facilitate fusion of bone segments and associated methods. Even more particularly, the disclosure relates to a spinal fusion implant configured for midline insertion, and related instruments.

BACKGROUND

The integrity of the spine, including its subcomponents like the vertebral bodies and intervertebral discs that are well known structural body parts forming the spine, are key to a patient's health. These parts may become crushed or damaged as a result of trauma or injury, or damaged by disease (e.g., by tumor, autoimmune disease) or as a result of wear over time or degeneration caused by the normal aging process.

In many instances, one or more damaged structural body parts can be repaired or replaced with a prosthesis or implant. For example, specific to the spine, one method of repair is to remove the damaged vertebra (in whole or in part) and/or the damaged disc (in whole or in part) and replace it with an implant or prosthesis. In some cases, it is necessary to stabilize a weakened or damaged spinal region by reducing or inhibiting mobility in the area to avoid further progression of the damage and/or to reduce or alleviate pain caused by the damage or injury. In other cases, it is desirable to join together the damaged vertebrae and/or induce healing of the vertebrae. Accordingly, an implant or prosthesis may be configured to facilitate fusion between two adjacent vertebrae. The implant or prosthesis may be placed without attachment means or fastened in position between adjacent structural body parts (e.g., adjacent vertebral bodies).

Typically, an implant or prosthesis is secured directly to a bone structure by mechanical or biological means. One manner of spine repair involves attaching a fusion implant or prosthesis to adjacent vertebral bodies using a fixation element, such as a screw. Most implants and their attachment means are configured to provide an immediate, rigid fixation of the implant to the implantation site. Unfortunately, after implantation the implants tend to subside, or settle, into the surrounding environment as the patient's weight is exerted upon the implant. In some cases, this subsidence may cause the rigidly fixed attachment means to either loosen, dislodge or potentially damage one or more of the vertebral bodies.

Several known surgical techniques can be used to implant a spinal prosthesis. The suitability of any particular technique may depend upon the amount of access available to the implant site. For instance, a surgeon may elect a particular entry pathway depending on the size of the patient or the condition of the patient's spine such as where a tumor, scar tissue, or other obstacle is present. Other times, it may be desirable to minimize intrusion into the patient's musculature and associated ligamentous tissue. In some patients who have had prior surgeries, implants or fixation elements may have already been inserted into the patient's spine, and as such, an implant introduction pathway may have to account for these prior existing conditions.

Thus, it is desirable to provide an implant that can be easily inserted in accordance with a specific pathway or approach. For example, in certain situations, it is desirable to provide a spinal implant that can be inserted using a midline approach. In addition, it is desirable to provide an implant and associated fixation elements that can account for subsidence that occurs with the implant subsequent to implantation while also providing rigid fixation.

SUMMARY

The embodiments provide a spinal implant that is configured for midline insertion into a patient's intervertebral disc space. The spinal implant may have a body including one or more apertures. The apertures are configured to receive fixation elements, such as bone screws and the like. The fixation element may comprise one or more anti-backout features, such as a split ring. The spinal implant may include structural guidance features to facilitate the angular approach of the fixation element into the apertures. The spinal implant may also be a configured with a tactile or visual feedback response feature to allow the user to know when the fixation elements are fully seated within the apertures.

The present disclosure describes a spinal implant that is configured for midline insertion into a patient's intervertebral disc space. In accordance with one exemplary embodiment, a spinal implant is provided having an upper surface, a lower surface, an anterior portion, a posterior portion and one or more apertures within the anterior portion for receiving at least one fixation element wherein the implant is configured for midline insertion. All or some of the apertures may be configured to permit a predetermined amount of nutation by a fixation element, thus allowing the fixation element to toggle from one position to another. The spinal implant may additionally include anti-migration features.

In another exemplary embodiment, a spinal implant comprises a body and one or more apertures. The body may comprise an upper surface, a lower surface, an anterior portion, and a posterior portion, wherein the body is configured for midline insertion between vertebral bodies of a patient's spine. The one or more apertures may be provided within the anterior portion of the body and can receive at least one fixation element. At least one of the apertures is configured with either a tactile or visual feedback response feature to allow the user to know when the at least one fixation element is fully seated. In one embodiment, the at least one aperture comprises a countersink with a center that is offset to the axis of the aperture.

In still another exemplary embodiment, a spinal implant comprises a body and one or more apertures. The body may comprise an upper surface, a lower surface, an anterior portion, and a posterior portion, wherein the body is configured for midline insertion between vertebral bodies of a patient's spine. The one or more apertures may be provided within the anterior portion of the body and can receive at least one fixation element. At least one of the apertures is configured with a structural guidance feature to facilitate approach of the at least one fixation element into the opening. In one embodiment, the structural guidance feature comprises a reverse chamfer over the at least one aperture.

In yet another exemplary embodiment, a method of treating a patient's spine comprises accessing at least a portion of a patient's spine via a posterior, midline approach. A spinal implant is then inserted between vertebral bodies of the patient's spine, wherein the spinal implant comprises a body having an upper surface, a lower surface, an anterior portion, a posterior portion, wherein the body is configured for midline insertion between vertebral bodies of a patient's spine, the implant further including one or more apertures within the anterior portion of the body for receiving at least one fixation element. The spinal implant is attached with the at least one fixation element to the vertebral bodies and a predetermined amount of toggling of the fixation element is permitted based on nutation of the fixation element during subsidence of the spinal implant.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIGS. 1A-1E show perspective views of an exemplary embodiment of a spinal implant of the present disclosure, in which:

FIG. 1A shows a perspective front view of the spinal implant;

FIG. 1B shows a top-down view of the spinal implant of FIG. 1A;

FIG. 1C shows a perspective rear view of the spinal implant of FIG. 1A;

FIG. 1D shows a cross-sectional view of the spinal implant of FIG. 1A; and FIG. 1E shows still another cross-sectional view of the spinal implant of FIG. 1A.

DESCRIPTION OF THE EMBODIMENTS

The present disclosure describes a spinal implant that is configured for midline insertion into a patient's intervertebral disc space. In accordance with one exemplary embodiment, a spinal implant is provided having an upper surface, a lower surface, an anterior portion, a posterior portion and one or more apertures within the anterior portion for receiving at least one fixation element wherein the implant is configured for midline insertion. All or some of the apertures may be configured to permit a predetermined amount of nutation by a fixation element, thus allowing the fixation element to toggle from one position to another. The spinal implant may additionally include anti-migration features.

Referring now to FIGS. 1A-1E, a spinal implant 10 of the present disclosure is shown. The spinal implant is configured for midline insertion into a patient's intervertebral disc space. The spinal implant 10 may be employed in the lumbar or thoracic regions. Alternatively, the spinal implant 10 may be employed in the cervical region of the spine. A cervical version may be provided so long as it is appropriately sized and configured, and the surgical approach takes into account this specific cervical design as well as size.

The spinal implant 10 may include anterior and posterior portions 12, 14 and upper and lower surfaces 16, 18 profiled to correspond with the intervertebral space to which they are to be secured. The upper and lower surfaces 16, 18 may further include surface enhancements 28, such as for example, teeth, ridges, protrusions, ribs, or fins, to enhance bone attachment, prevent migration and provide more stability. In one embodiment, the enhancements 28 may be formed at about a 30 degree angle with respect to the upper or lower surfaces 16, 18 of the implant 10. In other embodiments, the enhancements can have an angle between about 25 to about 35 degrees. It is understood, however, that alternative surface modifications, such as surface roughenings, barbs, spikes, bumps, etc., may also be employed. Further, biological agents, such as bone growth factors may be employed to enhance bone attachment, either alone or in combination with the mechanical enhancements described above.

Figure 1A:
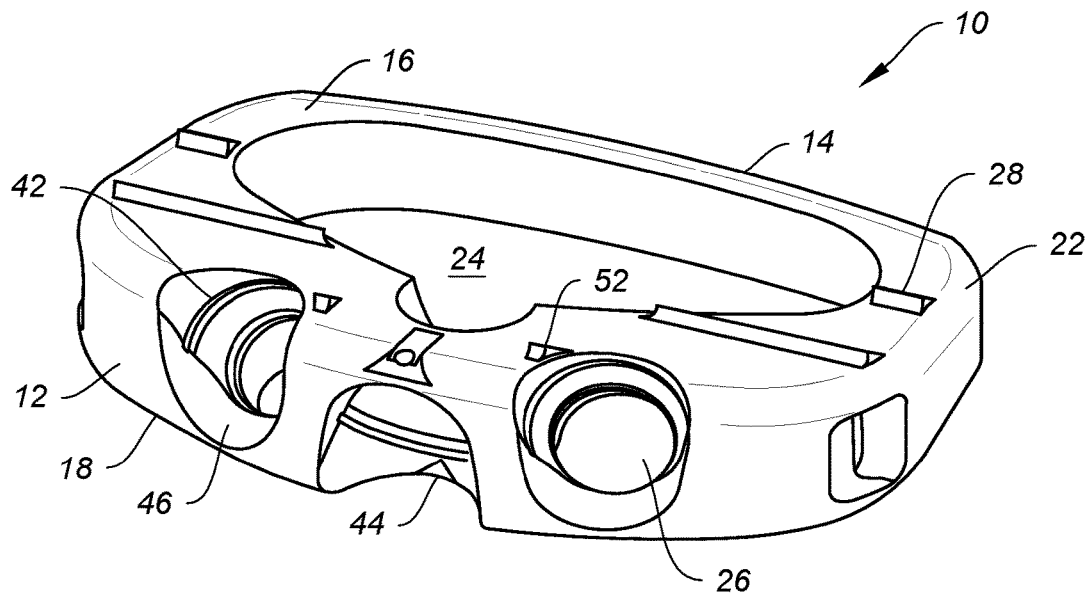
Figure 1B:
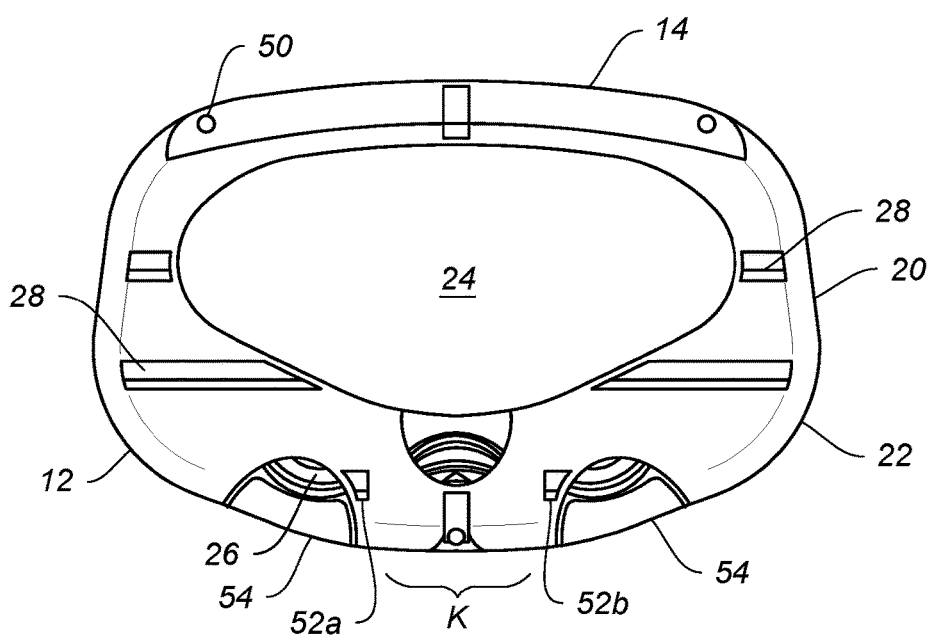
Figure 1C:
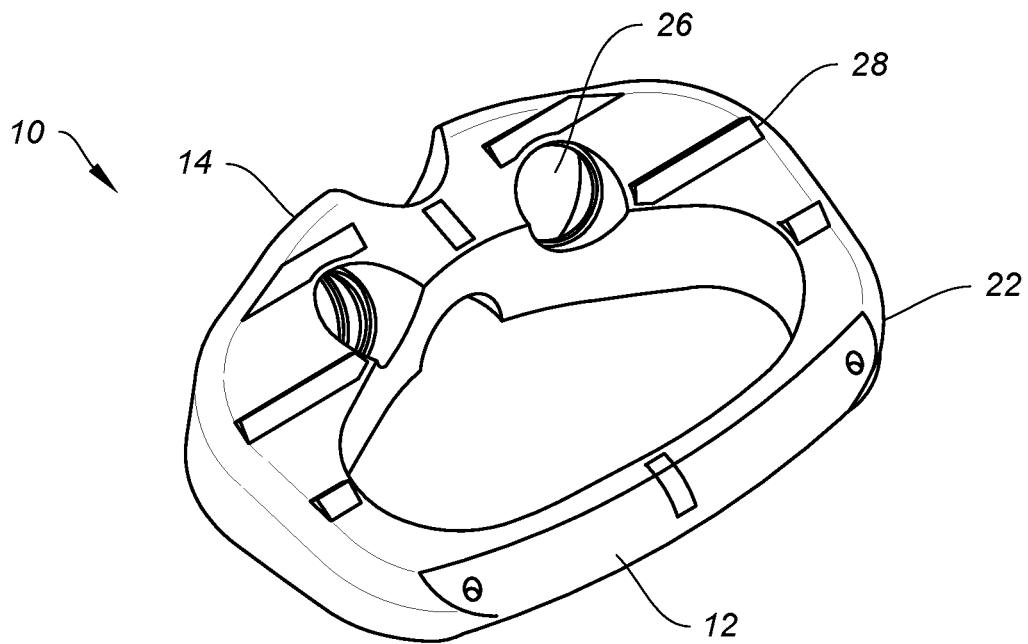
Figure 1D:
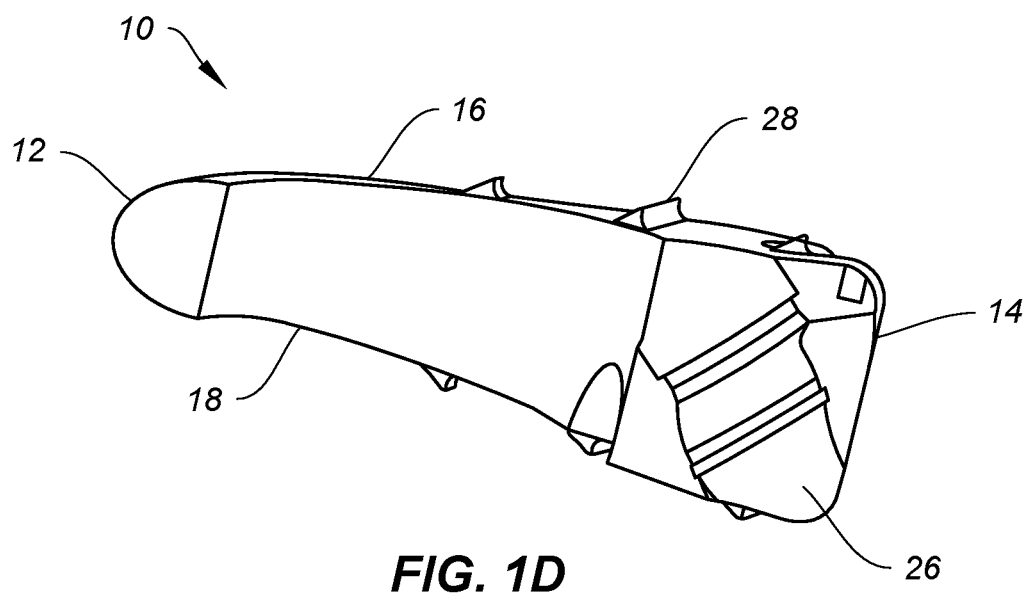

In one embodiment, as shown in FIGS. 1C and 1D, the spinal implant 10 defines a generally wedge shaped structure or arrowhead profile for ease of insertion and to be suitable for a posterior midline insertion approach. As can be seen in FIGS. 1B and 1D, the implant 10 may have rounded edges. The anterior portion 12 extends into curved sidewalls 20 that intersect with proximal portion 14 at posterolateral corners 22. The posterolateral corners may be rounded, as shown, to provide overall smoothness to the implant profile and prevent undesirable damage to surrounding tissue. The spinal implant 10, however, may have other shapes depending on the desired implantation site. Furthermore, edges of the implant 10 may be shaped so as to cooperate with insertion tools to minimize unintended distraction of the vertebral bodies between which the implant 10 is being positioned during implantation.

In one embodiment, projections 52 on the upper surface 16 of the implant 10 may be provided to facilitate insertion. For instance, these projections 52 may be used to direct a tool or instrument. As shown in FIG. 1B, in one embodiment a pair of projections 52a, 52b may be centrally provided on the upper surface 16 of the implant 10. The projections 52a, 52b form a key way K for directing an inserter/distractor instrument's blade, and serves as a guide for such instruments.

The spinal implant 10 and its components may be formed of any suitable medical grade material, such as biocompatible metals like stainless steel, titanium, titanium alloys, etc. or a medical grade plastic, such as polyetheretherketone (PEEK) or another radiolucent material, ultra high molecular weight polyethylene (UHMWPE), etc. If so desired, the implant 10 may also be formed of a bioresorbable material. The bioresorbable material may be osteoconductive or osteoinductive (or both).

As shown, the spinal implant 10 may include a central opening or lumen 24 extending between the upper and lower surfaces 16, 18 to facilitate bony ingrowth or fusion between adjacent bone segments, such as vertebral bodies. If so desired, the opening 24 may be used to receive and hold bone graft material, or other biologically active materials like bone cement, bone void filler, bone substitute material, bone chips, demineralized bone matrix, and other similar materials. The spinal implant 10 may be configured in a way that optimizes the opening 24 such that the ratio of the cage or implant structure to the load bearing area is as large as possible.

The spinal implant 10 may include holes 26 for placement of fixation screws 60 therethrough to secure the spinal implant 10 to adjacent bone tissue. In the embodiment shown, the implant 10 includes three holes 26, such as one hole being centrally located (i.e., along the center line), and two laterally located (i.e., beside the center line.) Without compromising stability, the lateral holes 26 should be located in a manner that avoids the need to retract vessels during surgery. It has been postulated that extended retraction of vessels during surgery may lead to greater chances for complications to the patient. The lateral holes 26 should also be positioned so as to provide easier visibility of the surrounding implantation site for the surgeon. In the present embodiment shown in FIG. 1B, the screw holes 26 are closely packed for easier access around vessels.

Figure 2:
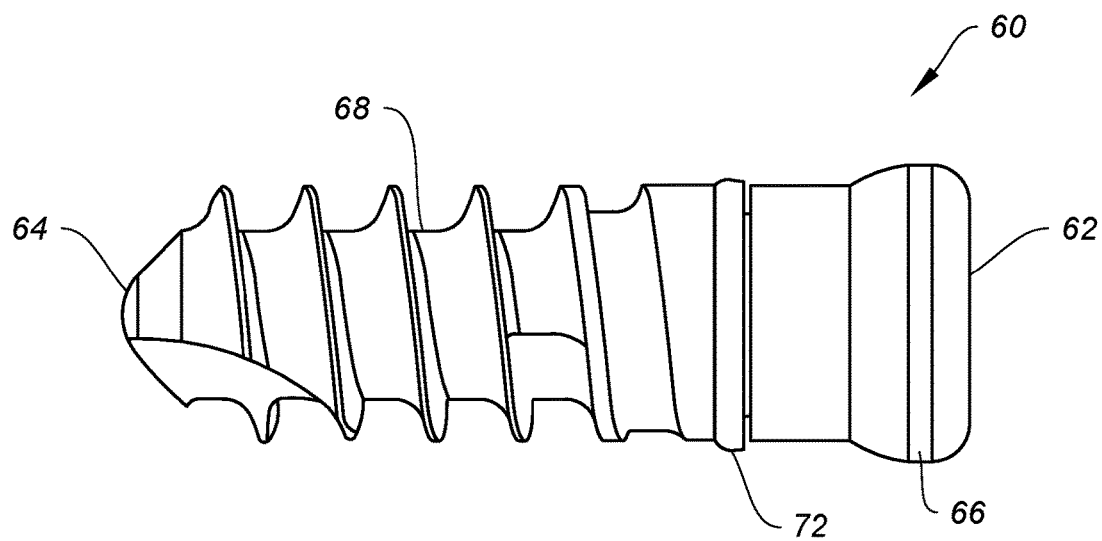
FIG. 2 illustrates a perspective side view of an exemplary embodiment of a fixation screw of the present disclosure.

FIG. 2 illustrates an exemplary fixation device such as a bone screw 60 that may be used with the implants 10 of the present disclosure. The bone screw 60 can have a head portion 62 and a tip 64 with a threaded shaft 68 in between. The bone screw 60 may also be used with an anti-backout ring 72. The screw 60 may also include a visual marker 66 comprising a groove, band, laser etching, or other similar physical indicator that disappears from view when the screw is fully seated, in order to assist with the insertion process. For example, during use, a groove or band 66 laser marked on the screw head 62 disappears from view when the screw 60 is fully seated within the screw hole 26 of the implant 10.

Figure 1E:
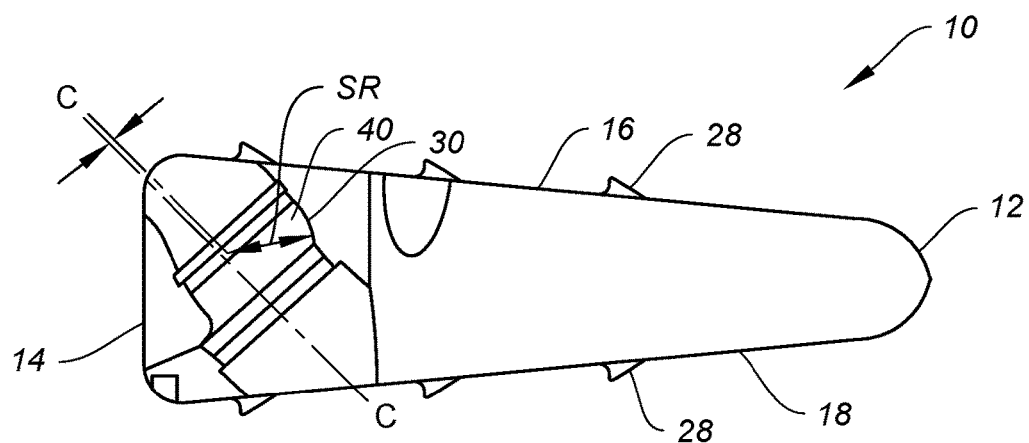

As shown in greater detail in FIGS. 1A, 1B and 1E, the holes 26 may also include visual cues or markers to provide visual feedback to the surgeon that a screw 60 inserted therein is properly seated. For example, in one embodiment, the visual cue may comprise a groove 42 around the screw hole 26, or an indicator arrow 44 that can be seen when the screw 60 is seated fully. In one aspect of the embodiment, the visual groove 42 may include an etching or a colored band. The visual groove 42 can be utilized to indicate that the screw 60 positioned therein is fully seated or implanted, thereby allowing the screw head 62 to clear the way for the user to view the groove 42. Similarly, the indicator arrows 44 may be utilized as visual checks by the user that the screws 60 are fully seated, as the arrows 44 would only be viewed upon fully seating the screws 60 after they have been placed into the screw holes 26. Accordingly, each of the screw holes 26 may be provided with one or more of these visual markers (i.e., a visual groove 42 or an indicator arrow 44, or both).

One skilled in the art will appreciate that the implant 10 may comprise any number of holes in any location on the implant 10. For instance, one embodiment of the spinal implant 10 may employ two of holes 26 that are located on either side of the center of implant 10. Optionally, the implant 10 may comprise other holes for receiving features like a radiologic marker or other imaging marker.

As shown in FIG. 1B, the spinal implant 10 may include bores 50 near the posterolateral corners 22 for receiving an imaging marker (not shown). The imaging marker may be formed of tantalum or a radiopaque material. The imaging marker may be configured as a rod or other appropriate shape. These imaging markers can assist with placement of the implant 10 by providing visual cues for the surgeon intraoperatively. A suitable imaging marker is disclosed in co-owned U.S. Pat. No. 8,870,961, entitled "SPINAL IMPLANT CONFIGURED FOR MIDLINE INSERTION," filed Nov. 8, 2010 and issued Oct. 28, 2014, the contents of which are incorporated herein by reference.

The holes 26 provide a path through which securing means (e.g., fixation elements such as bone screws) may be inserted so as to secure the implant 10 to respective superior and inferior vertebral bodies (not shown). The holes 26 may be configured to accommodate a variety of securing mechanisms, such as screws, pins, staples, or any other suitable fastening device.

The holes 26 of the spinal implant 10 may be configured to permit a predetermined amount of screw toggle (i.e., angular skew) and enable a lag effect when the fixation screw is inserted and resides inside the hole or lumen 26. In other words, the holes 26 may be designed to permit a certain degree of nutation by the screw, and thus, the screws may toggle from one position to one or more different positions, for instance, during subsidence. It also is believed that the predetermined screw toggle (permitted by the clearance between the lumen, or hole 26 and the screw) promotes locking of the screw to the implant 10 after subsidence subsequent to implantation. In one embodiment, the predetermined amount of screw toggle may be about 3 to 8 degrees, or about 5 to 6 degrees.

As shown in detail in FIG. 1E, each of the holes 26 may have an opening with a reverse chamfer or overhang feature. This overhang feature enable the surgeon to better guide the insertion and general approach of the fixation screw 60 into the screw hole 26. In addition the apertures 26 are configured not to break out onto the upper surface 16 of the implant 10, and as shown in FIG. 1B the anterior portion 12 has a flat face profile to better match the vertebral anatomy and which contacts bony endplates. As further shown in FIGS. 1A and 1B, the openings 26 may also include a relief 46, or cutaway portion, to promote visibility and ease of screw tip access. Moreover, the screw holes 26 may be provided on a flat face profile 54 of the implant 10, in order to better match the vertebral anatomy of the patient.

In one embodiment, the openings 26 may each include a countersink 40. The countersink feature's center is offset to the center axis of the hole 26, represented by lines C-C in FIG. 1E. This offset, represented by the arrows of FIG. 1E, allows a countervailing force when the surgeon applies pressure on the fixation screw 60 during insertion, and provides a tactile feedback response to let the surgeon know when the fixation screw's head 62 is properly seated. In other words, this offset causes the screw head 62 to become loaded (i.e., provide feedback) on final positioning.

As further shown, a portion of the countersink 40 may have a spherical surface 30. The position of the spherical surface may be defined by the spherical radius center (represented by arrowed line SR). In other embodiments, the openings or apertures 26 may be configured to provide a visual feedback response to the surgeon. Of course, the quality and strength of the feedback response also depends on the quality of the bone tissue at the area of treatment. Healthy normal bone tissue will obviously provide the best feedback, as unhealthy, diseased or damaged bone tissue would not have sufficient strength to provide the necessary countervailing force.

In one exemplary method of inserting the spinal implant 10, the surgeon prepares the implantation site by removing some disc material from the disc space between two adjacent vertebrae. The spinal implant 10 may be provided to the surgeon with the screws pre-attached, or separately, as desired. Using a posterior midline approach, the surgeon then places the implant 10 in the desired location of a patient's spine. Once in the correct location, the surgeon can tighten the screws into the surrounding bone tissue, thereby securing the implant 10.

As noted, the implant 10 may be configured to permit a predetermined amount of screw toggle and enable a lag effect when the fixation screw is inserted and resides inside the hole or lumen 26. Upon tightening, the lag effect may be observed whereby the implant 10 draws bone tissue towards itself, which may promote better fusion.

As further noted, the predetermined screw toggle promotes locking of the screw 60 to the implant 10 after subsidence subsequent to implantation. For example, after surgery, the patient's natural movement will result in settling and subsidence of bone tissue and the implant 10 in situ. It is believed that during this process, the weight exerted upon the implant 10 causes the fixation screws 60 to toggle and consequently lock against one or more surfaces of the holes 26 of the implant 10.

Some practitioners prefer to allow some degree of movement between the implant and the adjacent vertebral body after implantation. In that case the screw heads may be provided with contours on its underside as previously discussed that allow the screws to nutate and toggle with respect to the contoured holes 26 of the implant 10. Other practitioners may prefer a more rigid implant that is firmly locked to the adjacent vertebral body. The embodiments of implant 10 allow either preference.

In a rigidly fixed version, the screws may be provided without the contour on its underside (i.e., a relatively flat underside) while the opening 26 of the implant 10 would likewise not include a contoured seat or countersink 40. Thus, when secured together, the screws and implant 10 may form a rigidly locked construct. Where rigid fixation is desired (i.e., no toggle), the underside of the screws may also include surfaces features as well in order to provide secure attachment to the implant 10.

While a toggle and a rigidly fixed version of the implant 10 and screws 60 are described, it is understood that a combination of toggling and rigid fixation may be accomplished in a single implant 10 and attachment system. For example, it is possible to provide an implant 10 that allows toggling of one or more screws 60, while also allowing rigid fixation of the other of the screws.

It will also be appreciated that the angular positioning of the various holes, as described above, allows the present implant 10 to be of a relatively small size and therefore insertable from a midline approach within the intervertebral spaces of the spine. Thus, it will be appreciated that the angular positioning of the holes can assist effective operation of the implant 10 and the ability to "stack" implants in adjacent multilevel procedures without the securing means interfering with each other. Such a feature can be of major significance in some situations and applications.

As further noted, the predetermined screw toggle promotes locking of the screw to the implant 10 after subsidence subsequent to implantation. For example, after surgery, the patient's natural movement will result in settling and subsidence of bone tissue and the implant 10 in situ. It is believed that during this process, the weight exerted upon the implant 10 causes the fixation screws to nutate and/or toggle and eventually lock against one or more surfaces of the holes 26 of the implant 10.

Figure 3:
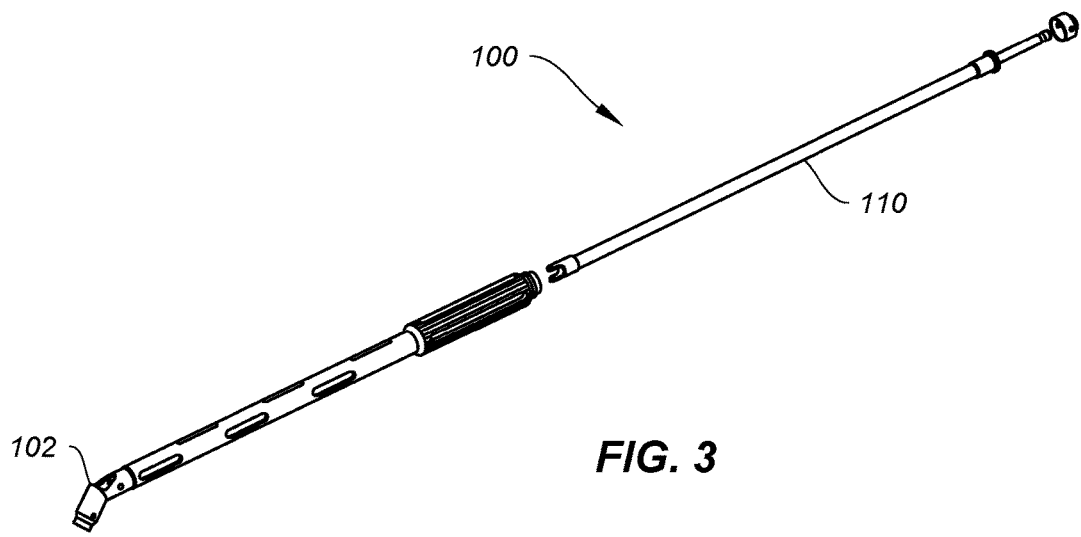
FIG. 3 illustrates an exploded view of an exemplary embodiment of a screwdriver of the present disclosure.
Figure 4A:
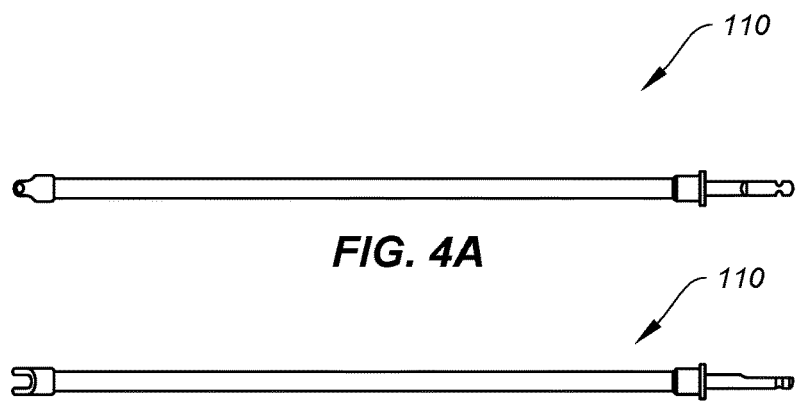
FIG. 4A illustrates a top-down view of the inner shaft of the screwdriver of FIG. 3.
Figure 4B:
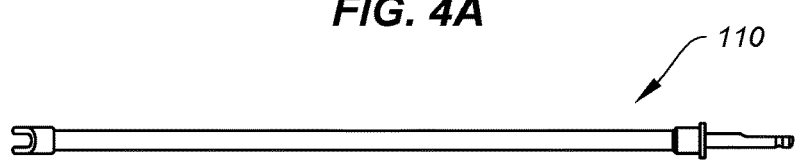
FIG. 4B illustrates a side perspective view of the inner shaft of FIG. 4A.
Figure 4C:
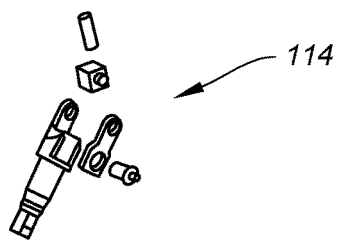
FIG. 4C illustrates an enlarged, exploded view of the universal joint of the screwdriver of FIG. 3.

The present disclosure also provides instruments that are useful for implanting the spinal implant 10 and for practicing the methods previously described. FIG. 3 shows an exemplary embodiment of a fixed angle screwdriver 100 of the present disclosure, and the inner shaft 110. FIGS. 4A and 4B show other perspective views of the inner shaft 110 of the screwdriver 100. As shown, the screwdriver 100 may have an angled neck portion 102 that has a fixed angle. FIG. 4C shows an enlarged and exploded view of the universal joint assembly 114 used with the inner shaft 110 within the screwdriver 100.

Figure 5A:
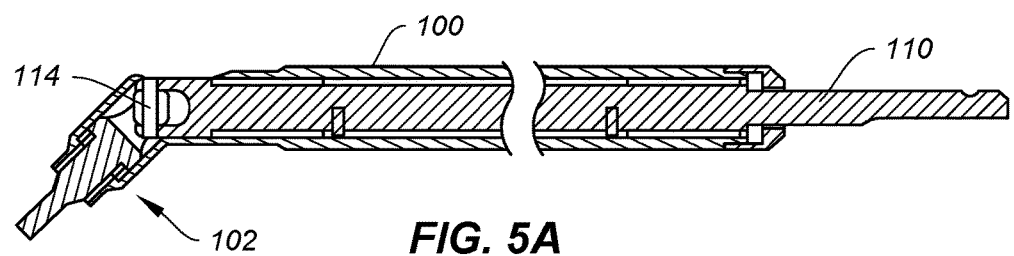
FIG. 5A illustrates a cross-sectional view of the screwdriver of FIG. 3.
Figure 5B:
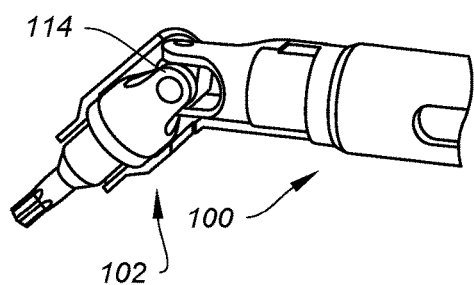
FIG. 5B illustrates a perspective view of a portion of the screwdriver of FIG. 3.

FIGS. 5A and 5B illustrate other views of the fixed angle screwdriver 100 that may be use in the lumbar region during the implantation process. As shown, the neck 102 of the screwdriver 100 may also be pre-bent and rigidly fixed. The universal joint assembly 114 promotes a more narrow diameter construct, without compromising strength, thereby providing the benefits of a single piece instrument that is minimally invasive. Moreover, the single piece instrument can be easily ported for cleanability.

Figure 6A:
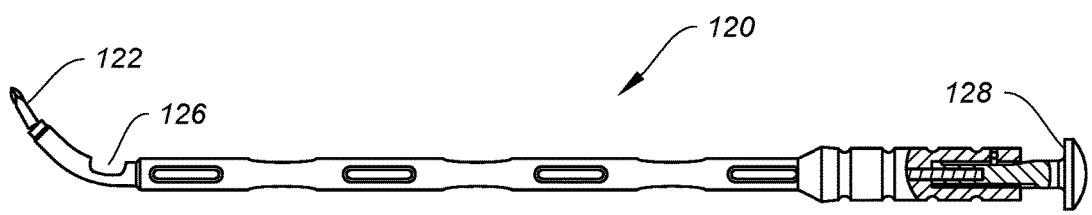
FIG. 6A illustrates a perspective view of an exemplary embodiment of an awl instrument with punch of the present disclosure.
Figure 6B:
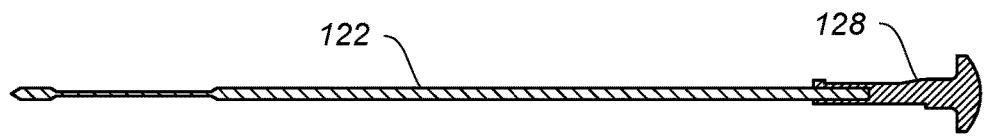
FIG. 6B illustrates a cross-sectional view of the awl instrument and punch of FIG. 6A.
Figure 7A:
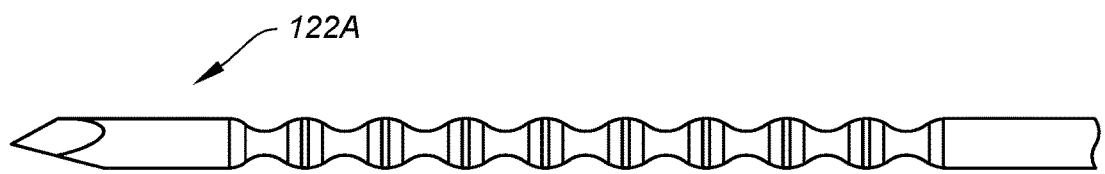
FIGS. 7A-7C illustrate perspective views of various designs for the punch of FIG. 6A.
Figure 7B:
Figure 7C:

FIGS. 6A and 6B illustrate exemplary embodiments of an angled guided awl 120 with punch 122 of the present disclosure. The punch 122 may extend in a handle or knob 128 to push the punch through the awl instrument 120, as shown in cross-section in FIG. 6B. The angled guided awl 120 can comprise a resected window 126 at an elbow of the instrument 120 to reduce drag and improve cleanability, as shown in FIG. 6A. Further, various wire or punch patterns and shapes may be employed to lower the force requirements for extension and retraction. These reduced surface area wires, or punches 122A, 122B, 122C, may have various configurations such as the ones shown in FIGS. 7A, 7B and 7C. The patterns of the exemplary punches/wires shown are configured to maintain flexibility and strength while reducing drag within the awl instrument 120.

Both the fixed angle screwdriver 100 and angled guided awl instrument 120 are configured to allow easy insertion of the implant 10 in the confined intervertebral space being treated. The slim profile and angularity of the instruments helps the surgeon navigate around the anatomy to properly position the implant 10 in a minimally invasive manner, without causing unneeded damage to the surrounding tissues.

Figure 8:
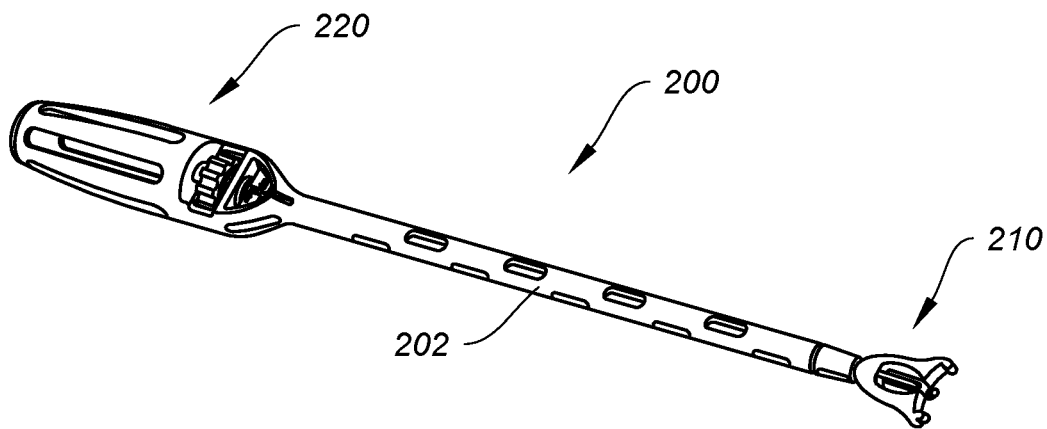
FIG. 8 illustrates a perspective view of an exemplary embodiment of a spinal implant inserter of the present disclosure.
Figure 9A:
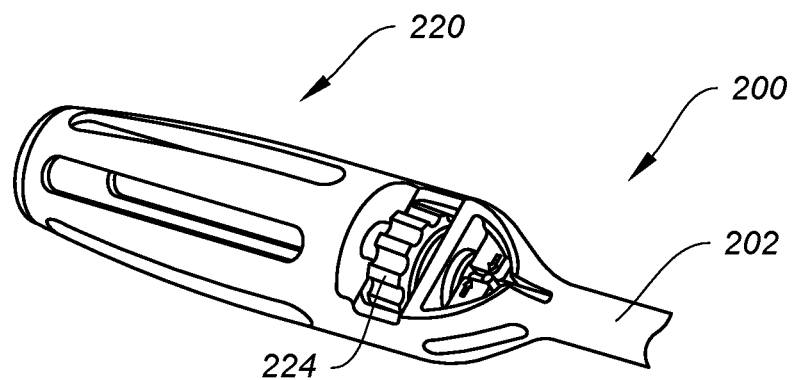
FIG. 9A illustrates an enlarged perspective view of a portion of the inserter of FIG. 8.
Figure 9B:
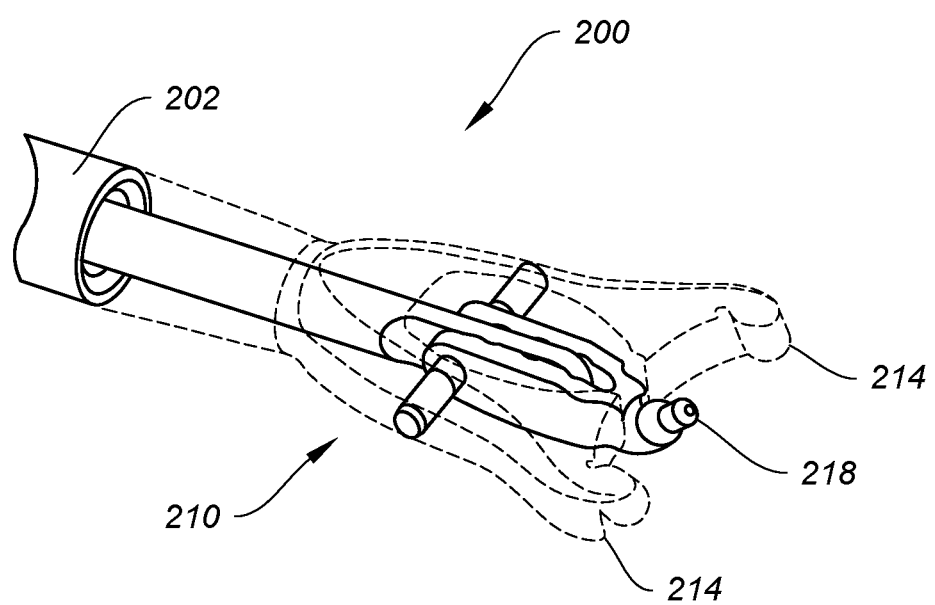
FIG. 9B illustrates a partial cutaway view of a portion of the inserter of FIG. 8.

FIG. 8 illustrates an exemplary embodiment of a spinal implant insertion instrument 200 of the present disclosure. The instrument 200 may comprise an elongate shaft 202 that extends between a gripping end 210 and a handle end 220. As shown in detail in FIG. 9A, the handle end 220 comprises a hand-controlled actuator or wheel 224 that controls movement at the gripping end 210. As FIG. 9B shows, the gripping end 210 comprises at least one fixed arm 214 for grabbing an opening 26 of the spinal implant 10. A movable arm 218 is also provided, which allows the user to securely hold the implant 10 during insertion. This movable arm 218 may be controlled by the actuator wheel 224, which can be turned left or right to effect movement of the movable arm 218 up and down, to engage with the central opening or hole 26 of the implant 10. One advantage of the actuator wheel 224 being positioned away from the terminal end of the handle end 220 is that the actuator wheel 224 is not in the way of the impaction end, which is the terminal end of the handle end 220.

Although the following discussion focuses on spinal implants or prostheses, it will be appreciated that many of the principles may equally be applied to other structural body parts within a human or animal body.

Other embodiments of the disclosure will be apparent to those skilled in the art from consideration of the specification and practice of the disclosure provided herein. It is intended that the specification and examples be considered as exemplary only.

What is claimed is:

1. A spinal implant insertion instrument comprising:
   a gripping end comprising first and second fixed arms for engaging first and second bone screw openings in a spinal implant, and a moveable third arm positioned between the first and second fixed arms for securely holding the spinal implant during insertion;
   a handle end comprising an actuator wheel for controlling movement at the gripping end; and
   an elongate shaft extending between said gripping end and said handle end;
   wherein rotation of the actuator wheel angularly moves the moveable third arm up and down to engage a third bone screw opening in the spinal implant.

2. The instrument of claim 1, wherein the moveable third arm is configured to pivot between the first fixed arm and the second fixed arm.

3. The instrument of claim 1, wherein the actuator wheel is positioned away from a terminal end of the handle end.

4. The instrument of claim 1, wherein the moveable third arm has an angled tip.

5. A method of using a spinal implant insertion instrument to securely hold a spinal implant during insertion, the method comprising:
   providing a spinal implant insertion instrument comprising a gripping end including first and second fixed arms, and a moveable third arm positioned between the first and second fixed arms, a handle end including an actuator wheel for controlling movement at the gripping end, and an elongate shaft extending between said gripping end and said handle end;
   engaging the first fixed arm with a first bone screw opening in the spinal implant;
   engaging the second fixed arm with a second bone screw opening in the spinal implant and
   rotating the actuator wheel to angularly move the moveable third arm up and down to engage a third bone screw opening in the spinal implant.

6. The method of claim 5, wherein the moveable third arm of the spinal implant insertion instrument pivots between the first fixed arm and the second fixed arm upon rotation of the actuator wheel.

7. The method of claim 5, wherein the third bone screw opening is a central opening located along a central axis of the spinal implant.

8. The method of claim 5, wherein the actuator wheel of the spinal implant insertion instrument is positioned away from a terminal end of the handle end.

9. The method of claim 5, wherein the moveable third arm of the spinal implant insertion instrument has an angled tip.

10. The instrument of claim 5, wherein the first and second fixed arms have rounded tips.

11. The instrument of claim 1, wherein the first and second fixed arms have rounded tips.

12. The instrument of claim 1, wherein the first and second fixed arms are curved along their length.

13. The instrument of claim 1, wherein the third movable arm is curved along its length.

14. The instrument of claim 4, wherein the angled tip comprises a protrusion for engaging the third bone screw opening of the spinal implant.

15. The instrument of claim 1, wherein the third bone screw opening is a central opening located along a central axis of the spinal implant.

* * * * *